(12) United States Patent
Kiani

(10) Patent No.: US 8,457,707 B2
(45) Date of Patent: Jun. 4, 2013

(54) CONGENITAL HEART DISEASE MONITOR

(75) Inventor: Massi E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 1422 days.

(21) Appl. No.: 11/858,053

(22) Filed: Sep. 19, 2007

(65) Prior Publication Data
US 2008/0071155 A1 Mar. 20, 2008

Related U.S. Application Data

(60) Provisional application No. 60/846,160, filed on Sep. 20, 2006.

(51) Int. Cl.
*A61B 5/1455* (2006.01)

(52) U.S. Cl.
USPC ............................ 600/324; 600/322; 600/323

(58) Field of Classification Search
USPC ................. 600/310, 316, 323–328, 335, 338, 600/340
See application file for complete search history.

(56) References Cited

U.S. PATENT DOCUMENTS

| | | | |
|---|---|---|---|
| 4,869,253 A * | 9/1989 | Craig et al. .................. | 600/323 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |

(Continued)

OTHER PUBLICATIONS

Hoke et al., "Oxygen saturation as a screening test for critical congenital heart disease: a preliminary study", Pediatr Cardiol 23:403-409, 2002.*

(Continued)

*Primary Examiner* — Eric Winakur
*Assistant Examiner* — Chu Chuan (JJ) Liu
(74) *Attorney, Agent, or Firm* — Knobbe Martens Olson & Bear LLP

(57) ABSTRACT

A congenital heart disease monitor utilizes a sensor capable of emitting multiple wavelengths of optical radiation into a tissue site and detecting the optical radiation after attenuation by pulsatile blood flowing within the tissue site. A patient monitor is capable of receiving a sensor signal corresponding to the detected optical radiation and calculating at least one physiological parameter in response. The physiological parameter is measured at a baseline site and a comparison site and a difference in these measurements is calculated. A potential congenital heart disease condition in indicated according to the measured physiological parameter at each of the sites or the calculated difference in the measured physiological parameter between the sites or both.

14 Claims, 10 Drawing Sheets

U.S. PATENT DOCUMENTS

| | | | |
|---|---|---|---|
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,239,905 B2 | 7/2007 | Kiani-Azarbayjany et al. | |

| | | |
|---|---|---|
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,894,868 B2 * | 2/2011 | Al-Ali et al. .......... 600/324 |

OTHER PUBLICATIONS

Granelli A.D., Mellander et al., "Screening for duct-dependent congenital heart disease with pulse oximetry: A critical evaluation of strategies to maximize sensitivity", *Acta Paediatrica*, 2005; 94:1590-1596, http://ww.masimo.com/pdf/Granelli_Article.pdf., 1 page downloaded and printed from the World Wide Web.

Koppel, Robert I et al., "Effective of Pulse Oximetry Screening for Congenital Heart Disease in Asymptomatic Newborns", *Pediatrics*, 2003, vol. 111, No. 3, 451-455.

* cited by examiner

CONGENITAL HEART DISEASE MONITOR

REFERENCE TO RELATED APPLICATION

The present application claims priority benefit under 35 U.S.C. §119(e) from U.S. Provisional Application No. 60/846,160, filed Sep. 20, 2006, entitled "Congenital Heart Disease Monitor," which is incorporated herein by reference.

BACKGROUND OF THE INVENTION

Congenital heart disease (CHD) is relatively common, occurring in 5 to 10 of every 1,000 live births. Early diagnosis and treatment has improved outcomes in this population, but still a number of infants with CHD are sent home undiagnosed. Up to 30% of deaths due to CHD in the first year of life are due to such unrecognized cases. Several forms of CHD are the result of a patent ductus arteriosus (PDA).

FIG. 1 illustrates a fetal heart 102 and a portion of a fetal lung 104. Prior to birth, the lung 104 is non-functional and fluid-filled. Instead, oxygenated blood is supplied to the fetus from gas-exchange in the placenta with the mother's blood supply. Specifically, oxygenated blood flows from the placenta, through the umbilical vein 106 and into the right atrium 122. There, it flows via the foramen 124 into the left atrium 152, where it is pumped into the left ventricle 150 and then into the aortic trunk 190. Also, oxygenated blood is pumped from the right atrium 122 into the right ventricle 120 and directly into the descending aorta 140 via the main pulmonary artery 180 and the ductus arteriosus 130. The purpose of the ductus arteriosus 130 is to shunt blood pumped by the right ventricle 120 past the constricted pulmonary circulation 110 and into the aorta 140. Normally, the ductus arteriosus 130 is only patent (open) during fetal life and the first 12 to 24 hours of life in term infants. If the ductus arteriosus remains patent, however, it can contribute to duct-dependent congenital heart diseases, such as those described below.

Patent Ductus Arteriosus

FIG. 2 illustrates a neonatal heart 202 with a patent ductus arteriosus 230. The ductus arteriosus frequently fails to close in premature infants, allowing left-to-right shunting, where oxygenated "red" blood flows from the aorta 240 to the now unconstricted pulmonary artery 210 and recirculates through the lungs 204. A persistent patent ductus arteriosus (PDA) results in pulmonary hyperperfusion and an enlarged right ventricle 220, which leads to a variety of abnormal respiratory, cardiac and genitourinary symptoms.

Persistent Pulmonary Hypertension in Neonates

As shown in FIG. 2, persistent Pulmonary Hypertension in Neonates (PPHN) is a neonatal condition with persistent elevation of pulmonary vascular resistance and pulmonary artery pressure. The pulmonary artery 210 that normally feeds oxygen depleted "blue" blood from the right ventricle 220 to the lung 204 is constricted. The back pressure from the constricted pulmonary artery 210 results in a right-to-left shunting of this oxygen depleted blood through the ductus arteriosus 230, causing it to mix with oxygen rich "red" blood flowing through the descending aorta 240.

Aortic Coarctation

Also shown in FIG. 2, coarctation of the aorta is a congenital cardiac anomaly in which obstruction or narrowing occurs in the distal aortic arch 290 or proximal descending aorta 240. It occurs as either an isolated lesion or coexisting with a variety of other congenital cardiac anomalies, such as a PDA. If the constriction is preductal, lower-trunk blood flow is supplied predominantly by the right ventricle 220 via the ductus arteriosus 230, and cyanosis, i.e. poorly oxygenated blood, is present distal to the coarctation. If the constriction is postductal, blood supply to the lower trunk is supplied via the ascending aorta 240.

SUMMARY OF THE INVENTION

Once a problematic patent ductus arteriosus (PDA) is detected, closure can be effected medically with indomethacin or ibuprofen or surgically by ligation. Clinical symptoms of duct-dependent CHD, however, can vary on an hourly basis, and the required extended and inherently intermittent testing is difficult with current diagnostic techniques. These techniques include physical examination, chest x-ray, blood gas analysis, echocardiogram, or a combination of the above to detect, as an example, the soft, long, low-frequency murmur associated with a large PDA or, as another example, a retrograde flow into the main pulmonary artery.

As shown in FIG. 2, a right hand has blood circulating from the left ventricle 250 through the innominate artery 260, which supplies the right subclavian artery (not shown). Because the innominate artery 260 is upstream from the ductus arteriosus 230, the oxygen saturation value and plethysmograph waveform obtained from the right hand are relatively unaffected by the shunt and serve as a baseline or reference for comparison with readings from other tissue sites. Alternatively, a reference sensor can be placed on a facial site, such as an ear, the nose or the lips. These sites provide arterial oxygen saturation and a plethysmograph for blood circulating from the left ventricle 250 to the innominate artery 260, which supplies the right common carotid artery (not shown), or to the left common carotid artery 265.

Also shown in FIG. 2, either foot has blood supplied from the descending aorta 240. A PDA 230 affects both the oxygen saturation and the blood flow in the descending aorta 240. As stated above, the PDA 230 causes oxygen-depleted blood to be mixed with oxygen-rich blood in the descending aorta 240. Because the descending aorta 240 supplies blood to the legs, the oxygen saturation readings at the foot will be lowered accordingly. That is, duct-dependent CHD may be manifested as a higher arterial oxygen saturation measured at a right hand tissue site (reference) and a lower oxygen saturation measured at a foot tissue site.

A PDA also allows a transitory left to right flow during systole, which distends the main pulmonary artery 280 as the result of the blood flow pressure at one end from the right ventricle and at the other end from the aortic arch 290. A left-to-right flow through the shunt 230 into the distended artery 280 alters the flow in the descending aorta 240 and, as a result, plethysmograph features measured at either foot. Duct-dependent CHD, therefore, may also be manifested as a plethysmograph with a narrow peak and possibly a well-defined dicrotic notch at a hand baseline site and a broadened peak and possibly no notch at a foot site.

Further shown in FIG. 2, a left hand has blood circulating from the left ventricle through the left subclavian artery 270 that supplies the left arm. Because the left subclavian artery 270 is nearer a PDA 230 than the further upstream innominate artery 260, it may experience some mixing of deoxygenated blood and an alteration in flow due to the PDA 230. Duct-dependent CHD, therefore, may also be manifested as a reduced saturation and an altered plethysmograph waveform measured at a left hand tissue site as compared with the right hand baseline site, although to a lesser degree than with a foot site.

FIG. 3 illustrates a patient monitoring system 300, which provides blood parameter measurements, such as arterial oxygen saturation, and which can be adapted as an advantageous diagnostic tool for duct-dependent CHD. The patient monitoring system 300 has a patient monitor 302 and a sensor 306. The sensor 306 attaches to a tissue site and includes a plurality of emitters 322 capable of irradiating a tissue site 320 with differing wavelengths of light, such as the red and infrared wavelengths utilized in pulse oximeters. The sensor 306 also includes one or more detectors 324 capable of detecting the light after attenuation by the tissue 320. A sensor is disclosed in U.S. application Ser. No. 11,367,013, filed on Mar. 1, 2006, titled Multiple Wavelength Sensor Emitters, which is incorporated by reference herein. Sensors that attach to a tissue site and include light emitters capable of irradiating a tissue site with at least red and infrared wavelengths are disclosed in one or more of U.S. Pat. Nos. 5,638,818, 5,782, 757, 6,285,896, 6,377,829, 6,760,607 6,934,570 6,985,764 and 7,027,849, incorporated by reference herein. Moreover, low noise optical sensors are available from Masimo Corporation, Irvine, Calif.

As shown in FIG. 3, the patient monitor 302 communicates with the sensor 306 to receive one or more intensity signals indicative of one or more physiological parameters and displays the parameter values. Drivers 310 convert digital control signals into analog drive signals capable of driving sensor emitters 322. A front-end 312 converts composite analog intensity signal(s) from light sensitive detector(s) 324 into digital data 342 input to the DSP 340. The DSP 340 may comprise a wide variety of data and/or signal processors capable of executing programs for determining physiological parameters from input data. In an embodiment, the DSP executes the CHD screening and analysis processes described with respect to FIGS. 7-9, below.

The instrument manager 360 may comprise one or more microcontrollers controlling system management, such as monitoring the activity of the DSP 340. The instrument manager 360 also has an input/output (I/O) port 368 that provides a user and/or device interface for communicating with the monitor 302. In an embodiment, the I/O port 368 provides threshold settings via a user keypad, network, computer or similar device, as described below.

Also shown in FIG. 3 are one or more devices 380 including a display 382, an audible indicator 384 and a user input 388. The display 382 is capable of displaying indicia representative of calculated physiological parameters such as one or more of a pulse rate (PR), plethysmograph (pleth) morphology, perfusion index (PI), signal quality and values of blood constituents in body tissue, including for example, oxygen saturation ($SpO_2$), carboxyhemoglobin (HbCO) and methemoglobin (HbMet). The monitor 302 may also be capable of storing or displaying historical or trending data related to one or more of the measured parameters or combinations of the measured parameters. The monitor 302 may also provide a trigger for the audible indictor 384 for beeps, tones and alarms, for example. Displays 382 include for example readouts, colored lights or graphics generated by LEDs, LCDs or CRTs to name a few. Audible indicators 384 include, for example, tones, beeps or alarms generated by speakers or other audio transducers to name a few. The user input device 388 may include, for example, a keypad, touch screen, pointing device, voice recognition device, or the like.

A patient monitor is disclosed in U.S. application Ser. No. 11,367,033, filed on Mar. 1, 2006, titled Noninvasive Multi-Parameter Patient Monitor, incorporated by reference herein. Pulse oximeters capable of measuring physiological parameters including $SpO_2$, pleth, perfusion index and signal quality are disclosed in one or more of U.S. Pat. Nos. 6,770,028, 6,658,276, 6,157,850, 6,002,952, and 5,769,785, incorporated by reference herein. Moreover, pulse oximeters capable of reading through motion induced noise are available from Masimo Corporation, Irvine, Calif.

A congenital heart disease (CHD) monitor advantageously utilizes a patient monitor capable of providing multiple-site blood parameter measurements, such as oxygen saturation, so as to detect, for example, hand-foot oxygen saturation differences associated with a PDA and related CHD.

One aspect of a CHD monitor is a sensor, a patient monitor and a DSP. The sensor is configured to emit optical radiation having a plurality of wavelengths into a tissue site and to detect the optical radiation after attenuation by pulsatile blood flowing within the tissue site. The monitor is configured to drive the sensor, receive a sensor signal corresponding to the detected optical radiation and to generate at least one of a visual output and an audio output responsive to the sensor signal. The DSP is a portion of the patient monitor and is programmed to derive a physiological parameter from sensor data responsive to the sensor signal. The physiological parameter is measured at a baseline tissue site and a comparison tissue site. The outputs indicate a potential CHD condition according to a difference between the physiological parameter measured at the baseline tissue site and the physiological parameter measured at the comparison tissue site.

Another aspect of a CHD monitor is a congenital heart disease screening method providing a patient monitor and corresponding sensor. The sensor is capable of emitting optical radiation having a plurality of wavelengths into a tissue site and detecting the optical radiation after attenuation by pulsatile blood flowing within the tissue site. The patient monitor is capable of receiving a sensor signal corresponding to the detected optical radiation and calculating a blood-related physiological parameter. The physiological parameter is measured at a baseline tissue site and a comparison tissue site. The measured physiological parameter at the baseline tissue site and at the comparison tissue site are compared. A potential CHD condition is indicated based upon the comparison.

A further aspect of a CHD monitor is a detection method determining a plurality of metrics responsive to sensor data derived from a plurality of tissue sites on an infant, testing the metrics with respect to predetermined rules and thresholds, and outputting diagnostics responsive to the test results. The metrics are at least one of a physiological parameter measurement, a cross-channel measurement and a trend. The diagnostics are responsive to the likelihood of congenital heart disease.

Yet another aspect of a CHD monitor comprises a patient monitor, a pre-processor means, an analyzer means and a post-processor means. The patient monitor is configured to receive sensor data from at least one optical sensor attached to a plurality of tissue sites on an infant. The pre-processor means is for deriving at least one metric from the sensor data. The analyzer means is for testing the at least one metric according to at least one rule. The post-processor means is for generating diagnostics based upon results of the testing The at least one rule defines when the at least one metric indicates a potential CHD condition in the infant.

DETAILED DESCRIPTION OF THE PREFERRED EMBODIMENTS

Figure 4:
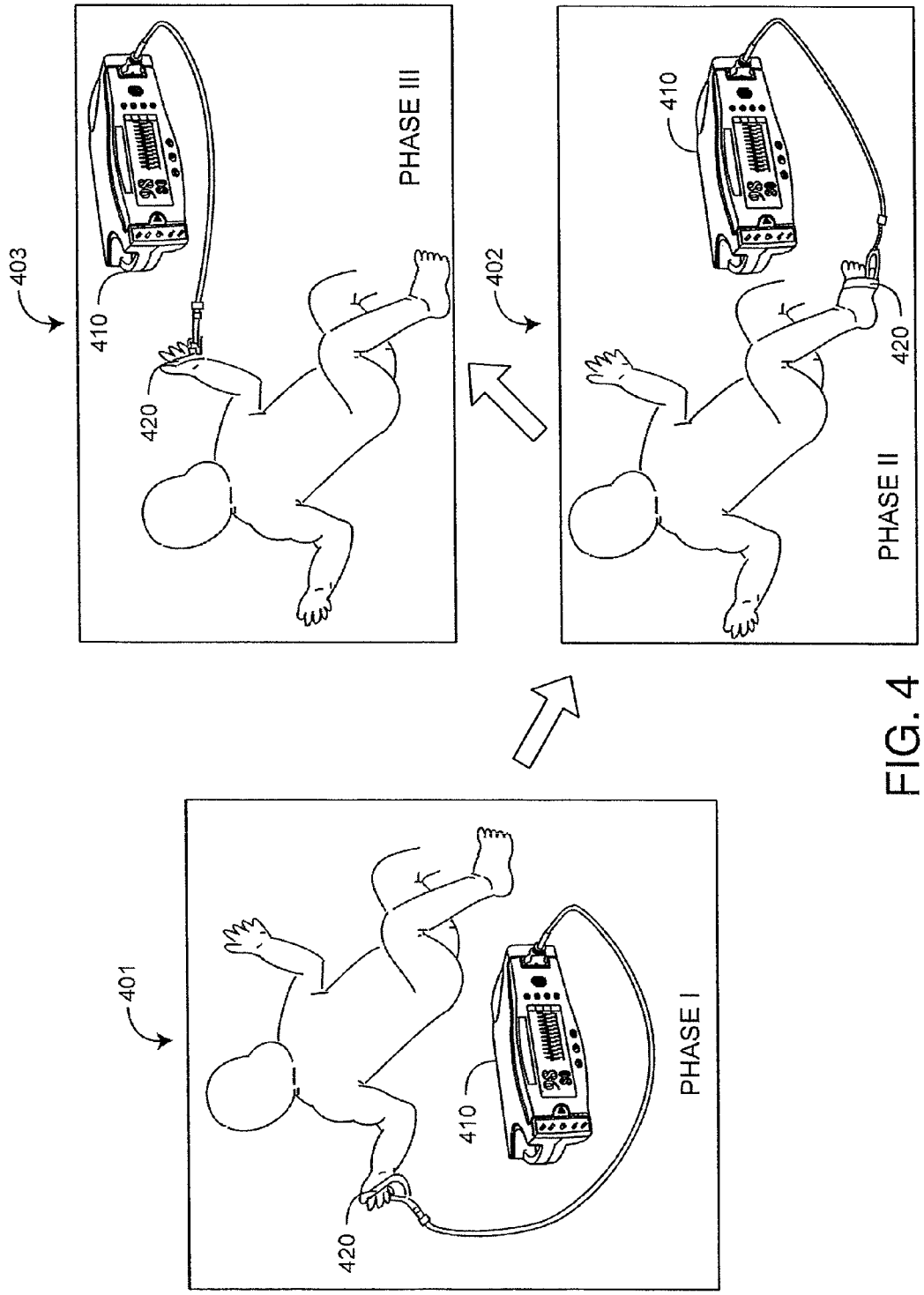
FIG. 4 is an illustration of a single patient monitor utilized for CHD detection.

FIG. 4 illustrates CHD detection utilizing a single patient monitor 410 and corresponding sensor 420. In general, the monitor 410 provides a display or other indicator that directs a caregiver or other user to attach the sensor 420 to an initial tissue site for a first measurement and then to one or more other tissue sites for additional measurements. This procedure is described in further detail with respect to FIGS. 7A-B, below. For example, in a Phase I configuration 401, the sensor 420 is attached to a neonate's right hand so that the monitor 410 generates baseline site measurements. In a Phase II configuration 402, the sensor 420 is attached to a neonate's foot so that the monitor 410 generates comparison site measurements. In an optional Phase III configuration 403, the sensor 420 is attached to a neonate's left hand generating measurements at an additional comparison site. During each phase 401-403, the monitor 410 takes measurements for a length of time sufficient to determine user-selected parameters, which includes $SpO_2$ and may include PR, PI, signal quality, pleth morphology, other blood parameters such as HbCO and HbMET, and trends over a selected time interval for any or all of these parameters. In an embodiment, baseline right-hand measurements are made first, followed by measurements at either foot, followed by optional left-hand measurements. In other embodiments, the phase-order of measurements can be user-selected and can be in any order and can include or exclude either the foot or the left-hand measurements.

In an embodiment, a monitor-determined time or user-selectable timer defines how long each site measurement is made, and a monitor display and/or audible indicator signals the user when to switch sensor sites. In an embodiment, a user defines time intervals or times-of-day for making repeat measurement cycles so as to obtain site difference trends. A monitor display and/or audible indicator signals the user when to begin a measurement cycle.

Figure 5:
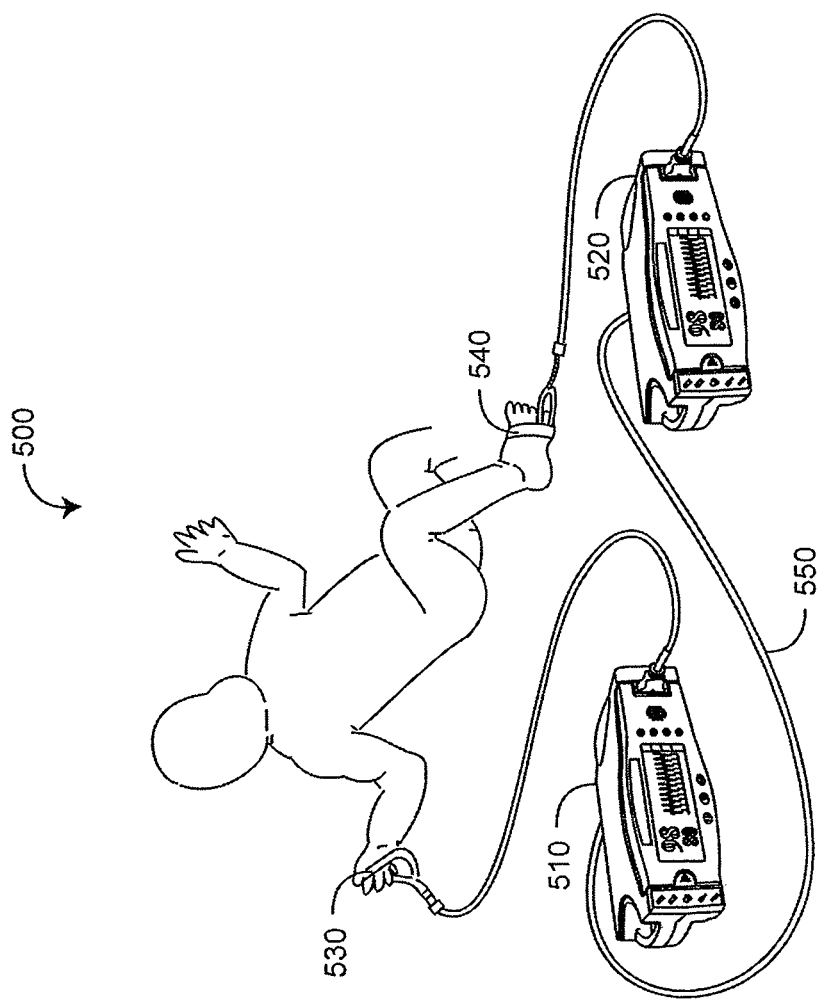
FIG. 5 is an illustration of multiple patient monitors utilized for CHD detection.

FIG. 5 illustrates CHD detection utilizing multiple patient monitors 510-520 and corresponding sensors 530-540. In an embodiment, a first monitor 510 and first sensor 530 provide measurements from a right-hand tissue site. A second monitor 520 and second sensor 540 provide measurements from a foot tissue site. An interface cable 550 or wireless link provides communications between the monitors 510-520. For example, the monitors 510-520 can communicate respective measurements via RS-232, USB, Firewire or any number of standard wired or wireless communication links. In an embodiment, one monitor, such as the baseline right-hand monitor 510 acts as the master and the comparison (e.g. foot) monitor 520 acts as a slave. The master monitor 510 generates the baseline measurements, transfers the comparison measurements from the slave monitor 520, calculates the comparison parameters, such as oxygen saturation differences, displays the comparison parameters, calculates alarm conditions based upon the measured and comparison parameters and generates alarms accordingly.

In other embodiments, the comparison site (e.g. foot or left-hand) monitor 520 is the master and the baseline (right-hand) monitor 510 is the slave. In yet another embodiment, there are three networked monitors corresponding to right-hand, left-hand and foot sites, with one monitor acting as a master and the other monitors acting as slaves. The master monitor, in this example, calculates oxygen saturation differences for each pair of sites and generates alarms accordingly.

Figure 6:
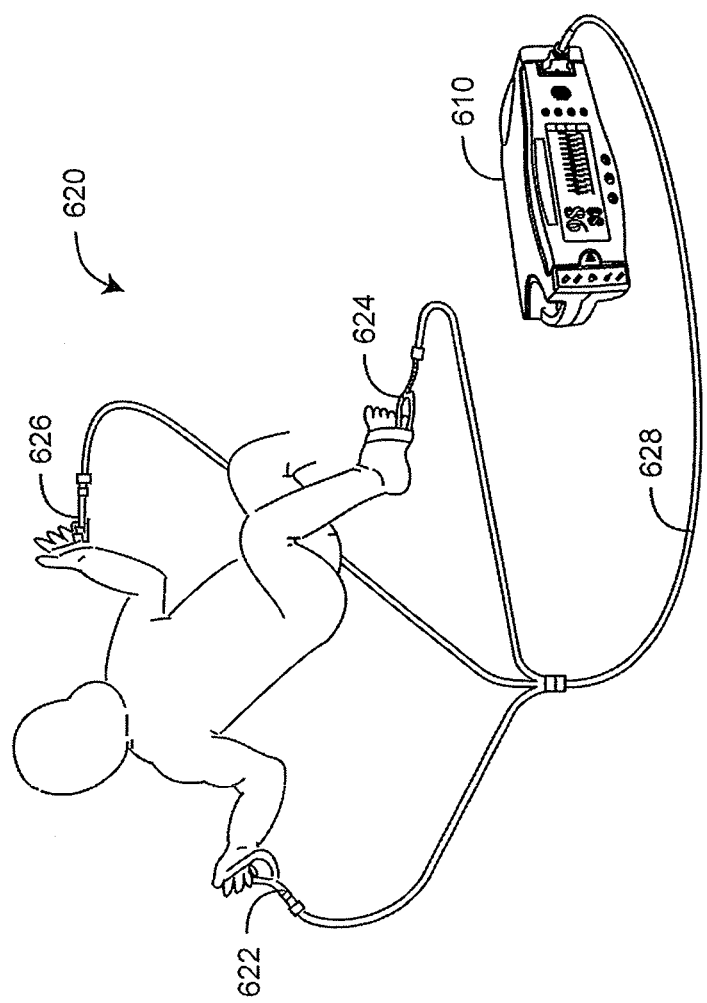
FIG. 6 is an illustration of a single patient monitor and multi-site sensor utilized for CHD detection.

FIG. 6 illustrates CHD screening utilizing a single CHD patient monitor 610 and a corresponding multi-site sensor 620. In an embodiment, the multi-site sensor 620 has two sensor heads 622-624 and a common sensor cable 628 for communication with the monitor 610. One sensor head 622 is attached to a baseline tissue site, e.g. a right-hand and another sensor head 624 is attached to a comparison tissue site, e.g. either a foot or a left-hand. In another embodiment, a third sensor head 626 is available for attachment to a second comparison site, e.g. a left-hand. A multiple site patient monitor is disclosed in U.S. Pat. No. 6,334,065 issued Dec. 25, 2001 titled Stereo Pulse Oximeter which is assigned to Masimo Corporation, Irvine, Calif. and incorporated by reference herein.

Figure 7A:
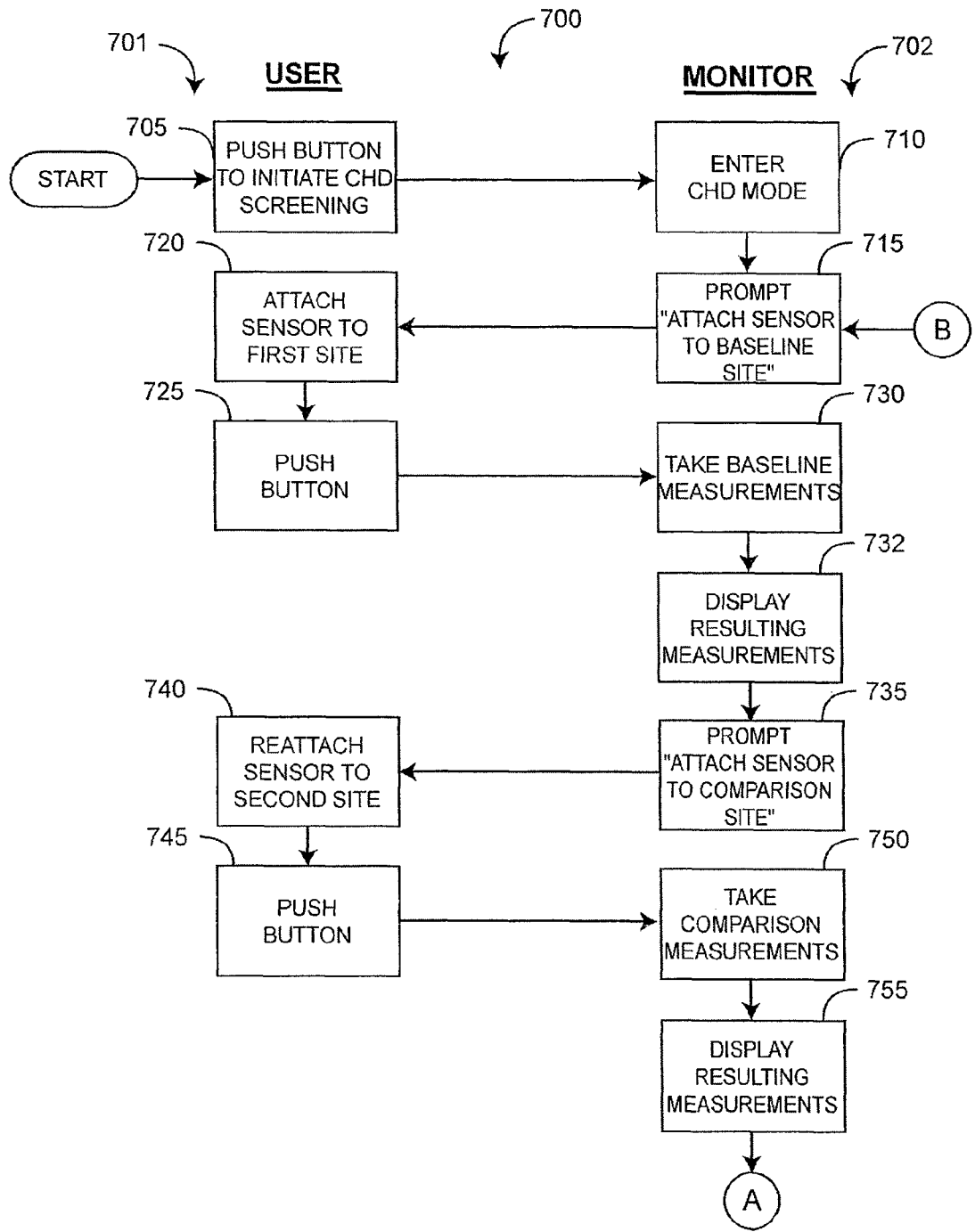
FIGS. 7A-B is a flow diagram of a CHD screening embodiment.
Figure 7B:
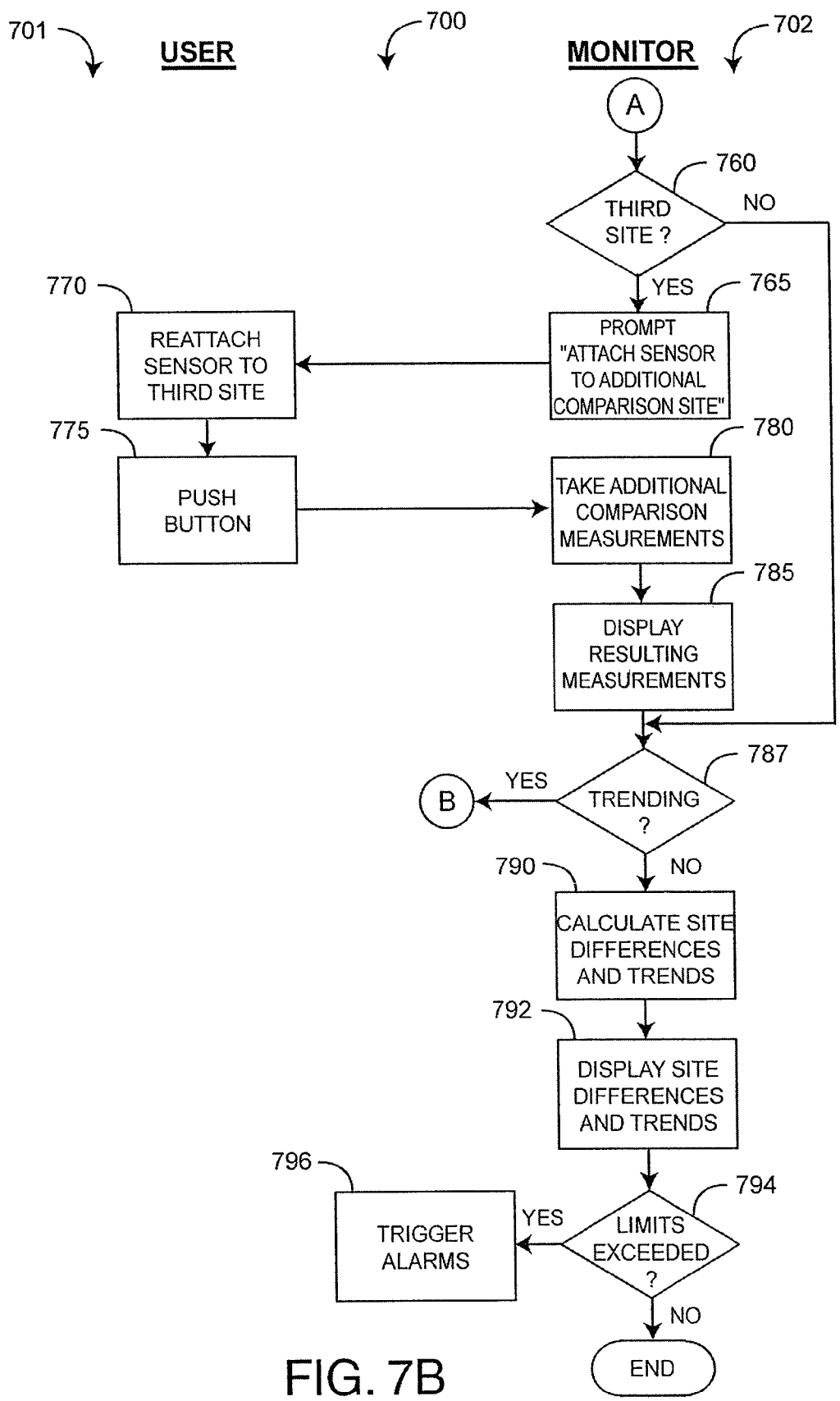

FIGS. 7A-B illustrate a CHD screening process 700 corresponding to a single monitor CHD detection embodiment, such as described with respect to FIG. 4, above. In general, the process 700 is described with respect to user actions 701 and monitor responses 702 and, likewise, monitor prompts 702 and user responses 701. In particular, once the monitor enters a CHD detection mode, the monitor prompts a user to attach the sensor successively to two or more tissue sites. In this manner, the monitor can compute baseline and comparison site measurements and calculate site differences, such as in oxygen saturation, which tend to predict the likelihood or unlikelihood of CHD. In an embodiment, the monitor 702 communicates instructions to the user 701 or otherwise prompts the user with display messages. Alternatively, or in addition to display messages, the monitor 702 can prompt the user via audio messages or indicators, visual indicators such as panel lights or a combination of the above. In an embodiment, the user 701 can trigger the monitor 702 or otherwise respond to monitor 702 prompts via a panel-mounted push button. Alternatively, or in addition to a push button, the user 701 can trigger the monitor 702 or otherwise respond to the monitor 702 via touch screen, touch pad, keyboard, mouse, pointer, voice recognition technology or any similar mechanism used for accomplishing a computer-human interface.

As shown in FIG. 7A, a user 701 initiates CHD screening 705 and the monitor 702 enters a CHD detection mode 710 in response. The monitor 702 then prompts the user 701 to attach a sensor to a baseline site 715. In response, the user 701 attaches a sensor to a first tissue site 720, such as a neonate's right hand, and pushes a button 725 to trigger the monitor to take baseline sensor measurements 730. The monitor 702 displays the resulting baseline measurements 732 and prompts the user 701 to reattach the sensor to a comparison site 735. In response, the user 701 removes the sensor and reattaches it to a second tissue site 740, such as either of a neonate's feet, and pushes a button 745 to trigger the monitor 702 to take comparison sensor measurements 750. The monitor 702 displays the resulting comparison site measurements 755.

As shown in FIG. 7B, after taking baseline site and comparison site measurements, the monitor 702 determines if a third site measurement is to be taken 760. If so, the monitor 702 prompts the user 701 to reattach the sensor to an additional comparison site 765. In response, the user 701 removes the sensor and reattaches it to a third tissue site 770, such as a neonate's left-hand, and pushes a button 775 to trigger the monitor 702 to take additional comparison site measurements 780. The monitor 702 then displays the resulting measurements 785. The monitor 702 determines if trend measurements are being made 787. If so, then after a predetermined delay the monitor 702 prompts the user to re-attach the sensor at the baseline site 715 (FIG. 7A) to begin an additional series of measurements 730-785.

Also shown in FIG. 7B, after all site measurements are taken, the monitor 702 calculates the measurement differences between the baseline and comparison site(s) 790, calculates trends in measurements and measurement differences 790 and displays the results 792. The monitor 702 then determines whether any site measurements, site measurement differences or trends are outside of preset limits 794. If limits are exceeded, the monitor generates visual and/or audio indicators of a potential CHD condition 796. For example, an audio alert or alarm of a potential CHD condition may be a low-level intermittent beep so as to indicate a diagnostic result and not be confused with other urgent care alarms. In one embodiment, if neonatal $SpO_2$ measurements from both a right hand and a foot are less than about 95% or a hand-foot difference is greater than about ±3%, the monitor generates one or more indicators alerting a caregiver that a potential CHD condition exists.

Figure 1:
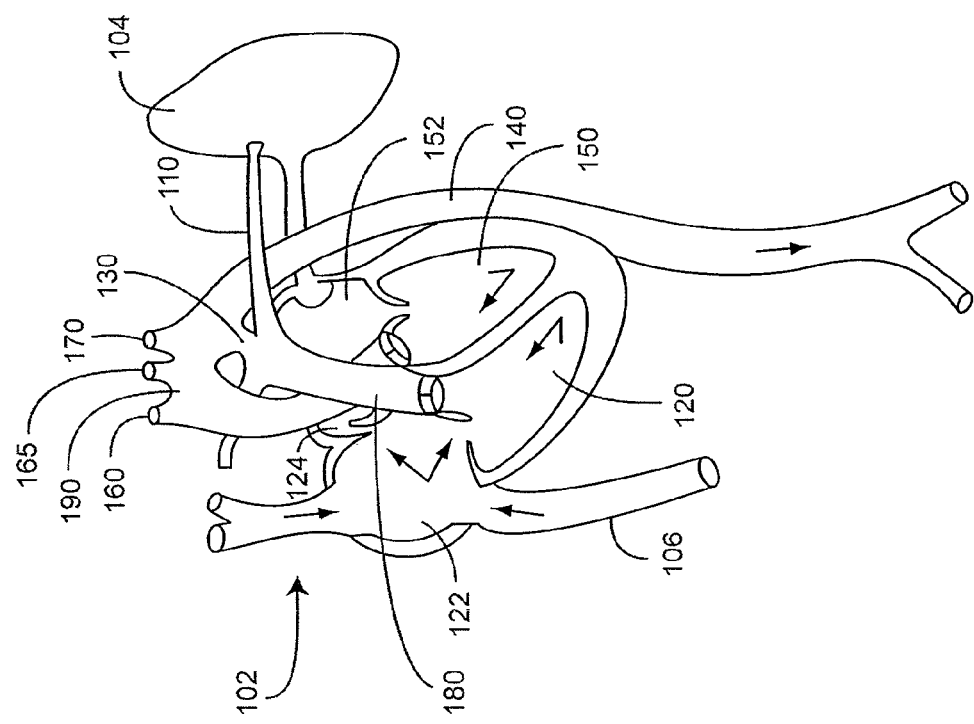
FIG. 1 is an illustration of a fetal heart depicting a ductus arteriosis.
Figure 2:
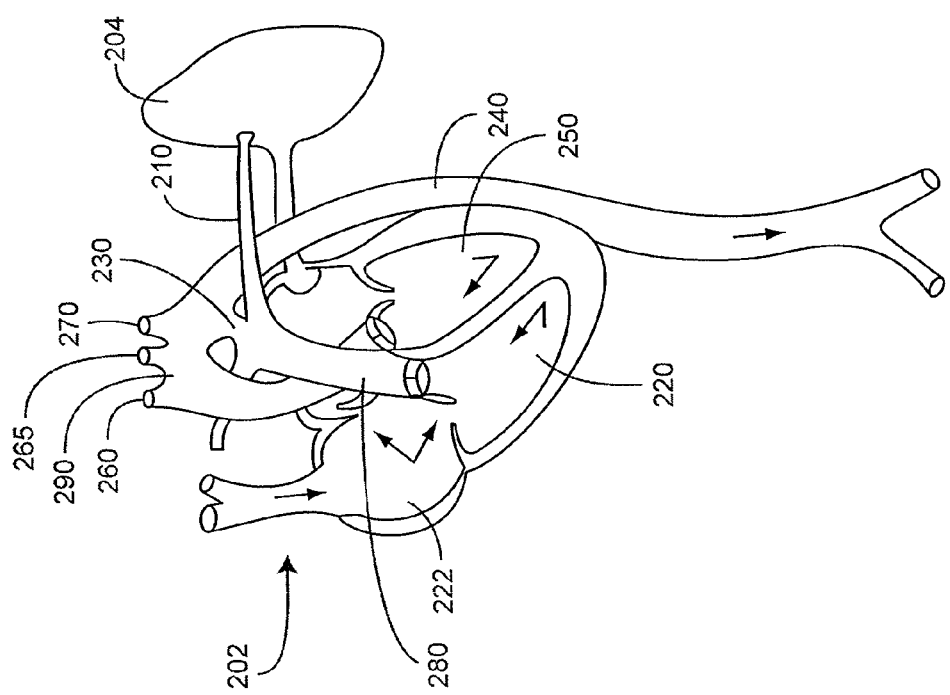
FIG. 2 is an illustration of a neonatal heart depicting a patent ductus arteriosis (PDA)
Figure 3:
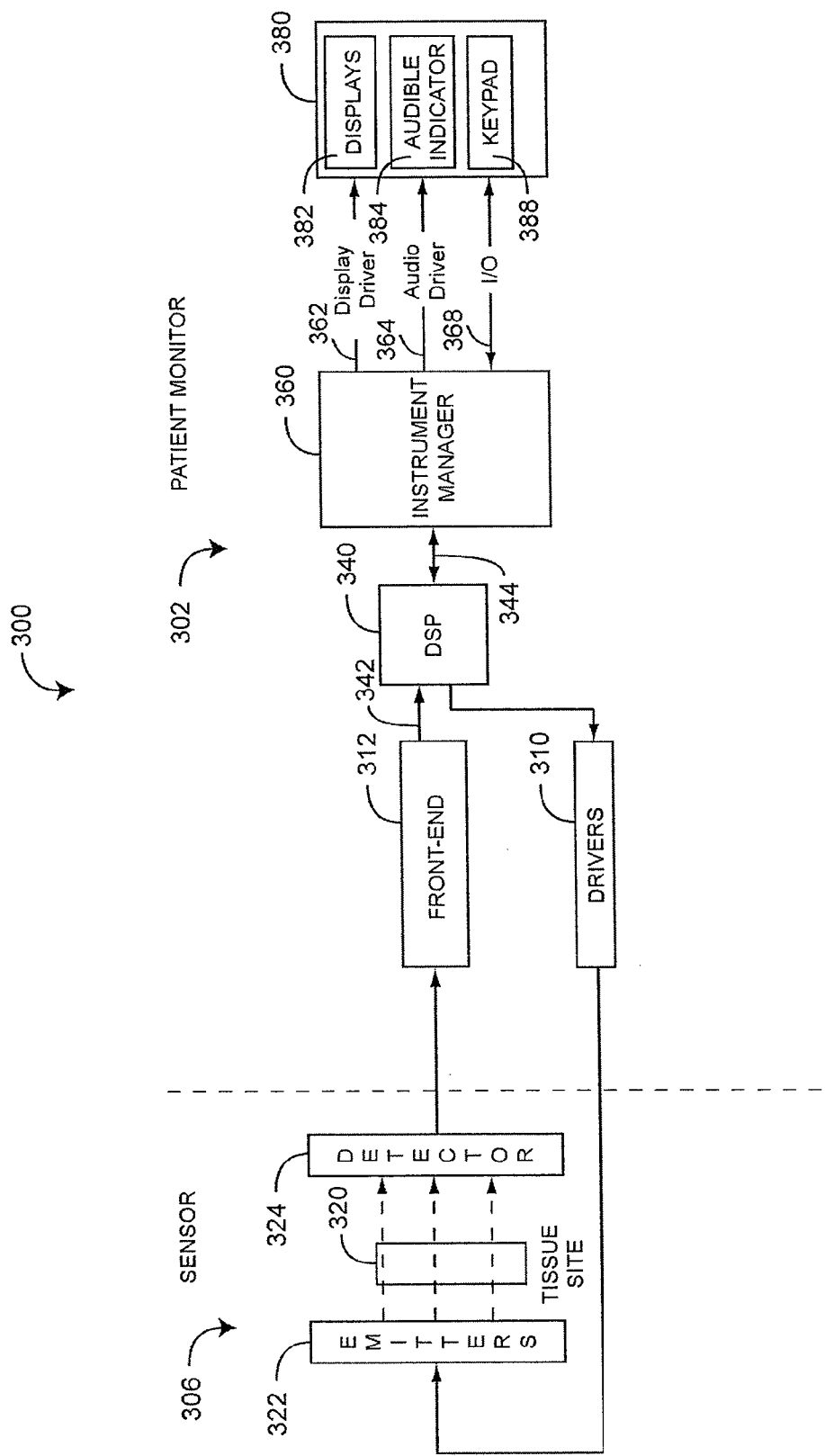
FIG. 3 is a general block diagram of a patient monitoring system adapted for congenital heart disease (CHD) detection.
Figure 8:
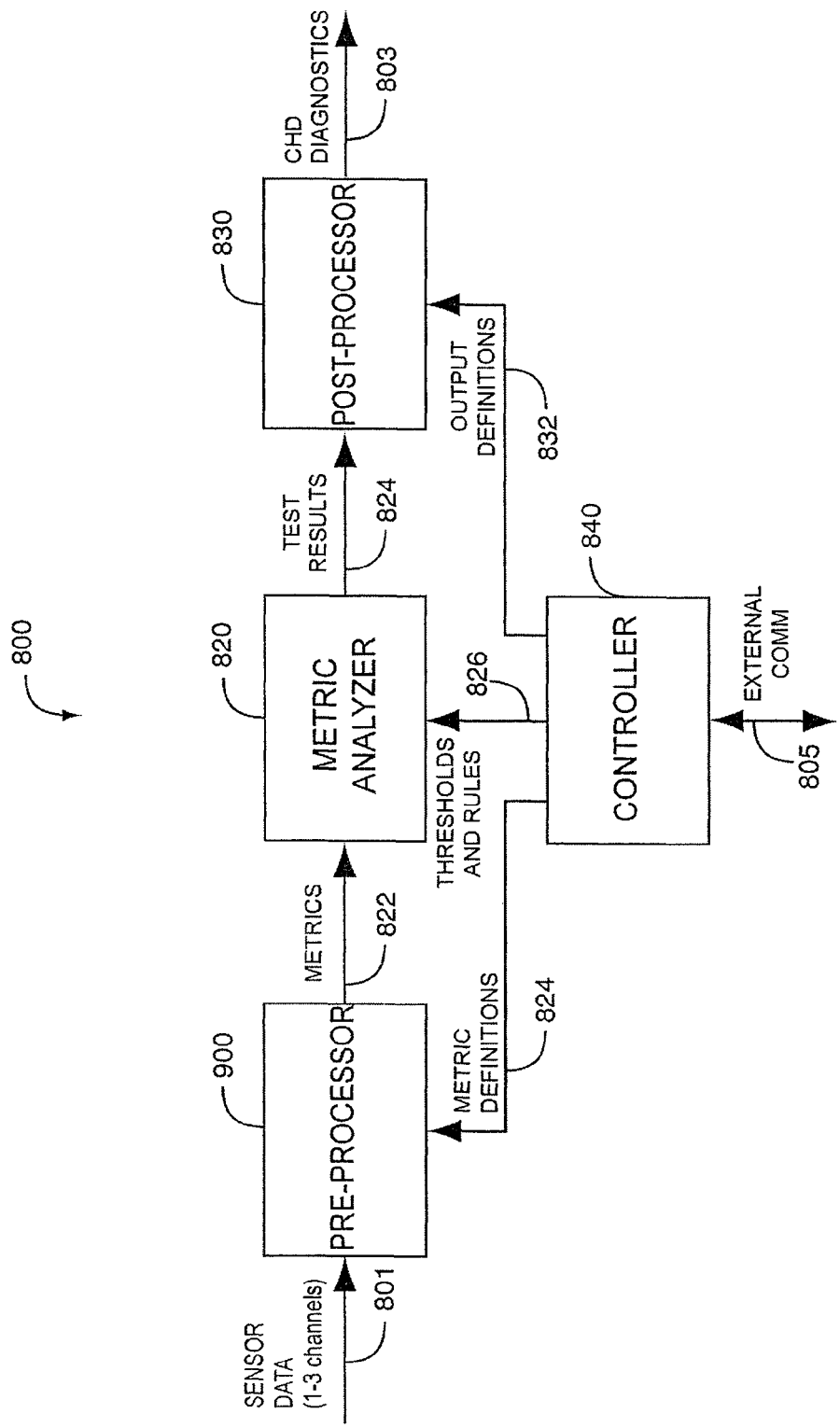
FIG. 8 is a detailed block diagram of a CHD analyzer embodiment.

FIG. 8 illustrates a CHD analyzer 800 that executes in the DSP 340 (FIG. 3) and indicates a potential CHD or lack thereof. The CHD analyzer 800 is advantageously responsive to multiple channels of sensor data 801 so as to generate CHD diagnostics 803. In an embodiment, the CHD analyzer 800 executes the CHD screening process described with respect to FIGS. 7A-B, above, receiving sensor data 342 (FIG. 3) derived from one tissue site at a time. In another embodiment, the CHD analyzer 800 receives sensor data 342 (FIG. 3) derived from two or more sensor sites at a time, such as described with respect to FIGS. 5-6, above. The diagnostic output 803 can be used, for example, to generate displays or indicators useful for grading a neonate with respect to a potential CHD condition and the severity of that condition. In an embodiment, an instrument manager 360 (FIG. 3) convert CHD diagnostics 803 via a display driver 362 (FIG. 3) and an audio driver 364 (FIG. 3) into one or more displays 382 (FIG. 3) and audible indicators 384 (FIG. 3) for use by a physician, clinician, nurse or other caregiver.

In an embodiment, the CHD analyzer 800 has a pre-processor 900, a metric analyzer 820, a post-processor 830 and a controller 840. The pre-processor 900 has sensor data inputs 801 from one or more sensor channels, such as described with respect to FIGS. 4-6, above. The pre-processor 900 generates metrics 822 that may include, for example, physiological parameters, waveform features, and cross-channel comparisons and trends, as described in further detail with respect to FIG. 9, below.

As shown in FIG. 8, the metric analyzer 820 is configured to test metrics 822 and communicate the test results 824 to the post-processor 830 based upon various rules applied to the metrics 822 in view of various thresholds 826. As an example, the metric analyzer 820 may communicate to the post-processor 830 when a parameter measurement increases faster than a predetermined rate, e.g. a trend metric exceeds a predetermined trend threshold.

Also shown in FIG. 8, the post processor 830 inputs test results 824 and generates CHD diagnostic outputs 803 based upon output definitions 832. For example, if the test result is that a trend metric exceeds a trend threshold, then the output definition corresponding to that test result may be to trigger an audible alarm. Thresholds, rules, tests and corresponding outputs are described in further detail with respect to TABLE 1, below.

Further shown in FIG. 8, the controller 840 has an external communications port 805 that provides predetermined thresholds, which the controller 840 transmits to the metric analyzer 820. The controller 840 may also provide metric definitions 824 to the pre-processor 900 and define outputs 832 for the post-processor 830.

In an embodiment, CHD screening grades a neonate with respect to a likelihood of a CHD condition utilizing green, yellow and red indicators. For example, a green panel light signals that no metric indicates a potential CHD condition exists. A yellow panel light signals that one metric indicates a potential CHD condition exists. A red panel light signals that more than one metric indicates that a potential CHD condition exists. In an embodiment, the CHD analyzer 800 provides a diagnostic output 803 according to TABLE 1, below. The terms $Sat_{xy}$, $\Delta Sat_{xy}$ and $\Delta t$ listed in TABLE 1 are described with respect to FIG. 9, below. Various other indicators, alarms, controls and diagnostics in response to various combinations of parameters and thresholds can be substituted for, or added to, the rule-based outputs illustrated in TABLE 1.

TABLE 1

CHD Analyzer Rules and Outputs

| RULE | OUTPUT |
| --- | --- |
| If Sat > Sat limit threshold (all channels); $Sat_{xy}$ < $Sat_{xy}$ limit threshold (all cross-channels); and $\Delta Sat_{xy}/\Delta t$ < $Sat_{xy}$ trend threshold (all cross-channels). | Then illuminate green indicator. |
| If Sat < Sat limit threshold (any channel); $Sat_{xy}$ > $Sat_{xy}$ limit threshold (any cross-channel); or $\Delta Sat_{xy}/\Delta t$ > $Sat_{xy}$ trend threshold (any cross-channel). | Then illuminate yellow indicator |
| If Sat < Sat limit threshold (any channel); and $Sat_{xy}$ > $Sat_{xy}$ limit threshold (any cross-channel). | Then illuminate red indicator |
| If Sat < Sat limit threshold (any channel); and $\Delta Sat_{xy}/\Delta t$ > $Sat_{xy}$ trend threshold (any cross-channel). | Then illuminate red indicator |

Figure 9:
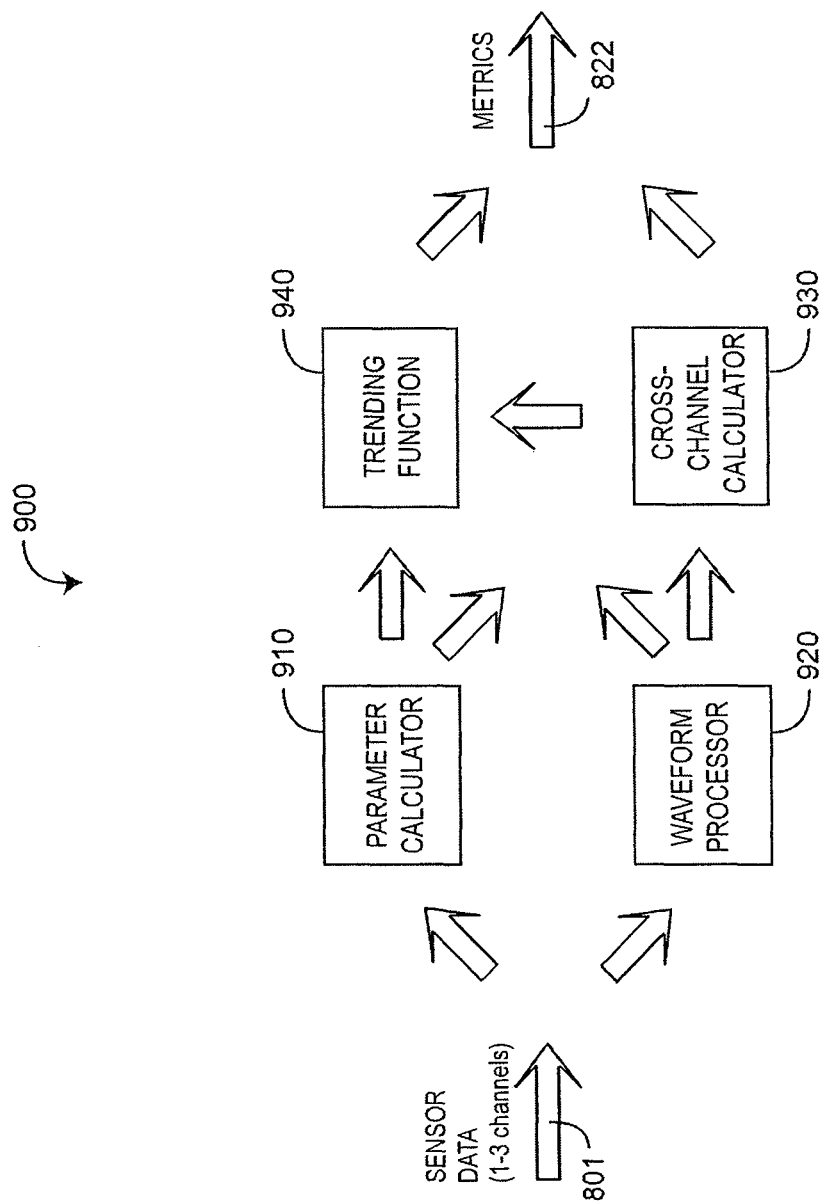
FIG. 9 is a detailed block diagram of a preprocessor embodiment for a CHD analyzer.

FIG. 9 illustrates a preprocessor embodiment 900 that inputs sensor data 801 derived from one or more tissue sites and outputs metrics 822. The preprocessor 900 has a parameter calculator 910, a waveform processor 920, a cross-channel calculator 930 and a trending function 940. The parameter calculator 910 outputs one or more physiological parameters derived from pulsatile blood flow at a tissue site. These parameters may include, as examples, arterial oxygen saturation ($SpaO_2$), venous oxygen saturation ($SpvO_2$), PR and PI to name a few. In an embodiment, the parameter calculator 910 generates one or more of these parameters for each sensor data channel. The waveform processor 920 extracts various plethysmograph features for each data channel. These features may include, for example, the area under the peripheral flow curve, the slope of the inflow phase, the slope of the outflow phase, the value of the end diastolic baseline and the size and location of the dicrotic notch. The cross-channel calculator 930 generates cross-channel values, such as $Sxy=SpO_2(\text{baseline site})-SpO_2(\text{comparison site})$. In an embodiment, the calculator 930 can also generate same-channel values, such as $SpaO_2-SpvO2$ from the same sensor site. The trending function 940 calculates trends from the parameter calculator 910, the waveform processor 920 or the cross-channel calculator 930. The trending function 940 stores historical values and compares these with present values. This comparison may include $\Delta p/\Delta t$, the change in a parameter over a specified time interval, which may also be expressed as a percentage change over that interval. An example is $\Delta Sat_{xy}/\Delta t$, the change in the oxygen saturation difference between two tissue sites over a specified time interval.

Although described above with respect to optical sensor inputs responsive to pulsatile blood flow, in an embodiment, the CHD monitor may include sensor inputs and corresponding algorithms and processes for other parameters such as ECG, EEG, $ETCO_2$, respiration rate and temperature to name a few. Although a CHD analyzer is described above as a program executed by a patient monitor DSP, the CHD analyzer can be, in whole or in part, hardware, firmware or software or a combination functioning in conjunction with or separate from the DSP. Further, the CHD analyzer can be configured, in whole or in part, as logic circuits, gate arrays, neural networks or an expert system, as examples. In an embodiment, a CHD monitor, such as described above, for example, as incorporating a patient monitor, CHD analyzer and corresponding CHD screening process, is marketed with instructions on grading a neonate, infant or patient with respect to the likelihood of a CHD condition.

A congenital heart disease monitor has been disclosed in detail in connection with various embodiments. These embodiments are disclosed by way of examples only and are not to limit the scope of the present invention, which is defined by the claims that follow. One of ordinary skill in the art will appreciate many variations and modification.

What is claimed is:

1. A congenital heart disease monitor comprising:
   a sensor including a plurality of light emitters configured to emit optical radiation having a plurality of wavelengths into a tissue site and a detector configured to detect the optical radiation after attenuation by pulsatile blood flowing within the tissue site;
   a patient monitor configured to drive the sensor, receive a sensor signal corresponding to the detected optical radiation and to generate at least one of a visual output and an audio output responsive to the sensor signal; and
   a digital signal processor within the patient monitor programmed to derive an oxygen saturation from sensor data responsive to the sensor signal,
   wherein the oxygen saturation is measured first at a baseline tissue site using the sensor including the plurality of light emitters and the detector and second at a comparison tissue site using the same sensor including the same plurality of light emitters and detector,
   wherein the processor is configured to determine a difference in oxygen saturation measurements between the baseline tissue site and the comparison tissue site, the difference measured over a time interval so as to determine a trend, the processor further configured to compare a trend slope to a trend threshold; and
   wherein at least one of the outputs indicates a potential congenital heart disease condition according to results of the comparison.

2. The congenital heart disease monitor according to claim 1 further comprising a congenital heart disease analyzer programmed in the digital signal processor, the analyzer comprising:
   a preprocessor configured to output metrics responsive to sensor data;
   a metric analyzer configured to test the metrics against predetermined rules; and
   a postprocessor configured to output diagnostics responsive to the test results,
   wherein the diagnostics are indicative of a potential congenital heart disease condition.

3. The congenital heart disease monitor according to claim 2:
   wherein the metrics comprise an oxygen saturation difference between tissue sites, and
   wherein the metric is tested to determine if the oxygen saturation difference exceeds a threshold.

4. The congenital heart disease monitor according to claim 1 wherein the visual output comprises a plurality of colored indicators that, when illuminated, signal different likelihoods that the oxygen saturation measurements have detected a congenital heart disease condition.

5. The congenital heart disease monitor according to claim 4 further comprising instructions on grading an infant as to the potential for congenital heart disease based upon one or more of the visual and audio outputs.

6. A method of monitoring a patient comprising the steps of:
   emitting optical radiation having a plurality of wavelengths into a tissue site using a sensor;
   detecting the optical radiation after attenuation by pulsatile blood flow within the tissue site using a detector;
   deriving an oxygen saturation measurement from sensor data responsive to the detected radiation;
   wherein the oxygen saturation is measured first at a baseline tissue site using the sensor including the plurality of light emitters and the detector and second at a comparison tissue site using the same sensor including the same plurality of light emitters and detector,
   determining a difference in oxygen saturation measurements between the baseline tissue site and the comparison tissue site, the difference measured over a time interval so as to determine a trend, and further comparing a trend slope to a trend threshold; and
   indicating a potential congenital heart disease condition according to results of the comparison.

7. The method of claim 6 further comprising the steps of:
   outputting metrics responsive to the sensor data;
   testing the metrics against predetermined rules; and
   outputting diagnostics responsive to the test results,
   wherein the diagnostics are indicative of a potential congenital heart disease condition.

8. The method of claim 7 wherein the metrics comprise an oxygen saturation difference between tissue sites and wherein the metrics are tested to determine if the oxygen saturation difference exceeds a threshold.

9. The method of claim 6 further comprising displaying a plurality of colored indicators that, when illuminated, signal different likelihoods that the oxygen saturation measurements have detected a congenital heart disease condition.

10. A congenital heart disease monitor comprising:
    means for emitting optical radiation having a plurality of wavelengths into a tissue site using a sensor;
    means for detecting the optical radiation after attenuation by pulsatile blood flow within the tissue site using a detector;
    means for deriving an oxygen saturation measurement from sensor data responsive to the detected radiation;
    wherein the oxygen saturation is measured first at a baseline tissue site using the sensor including the plurality of light emitters and the detector and second at a comparison tissue site using the same sensor including the same plurality of light emitters and detector,
    means for determining a difference in oxygen saturation measurements between the baseline tissue site and the comparison tissue site, the difference measured over a time interval so as to determine a trend, and further comparing a trend slope to a trend threshold; and means for indicating a potential congenital heart disease condition according to results of the comparison.

11. The monitor of claim 10 further comprising the steps of:
   means for outputting metrics responsive to the sensor data;
   means for testing the metrics against predetermined rules; and
   means for outputting diagnostics responsive to the test results,
   wherein the diagnostics are indicative of a potential congenital heart disease condition.

12. The monitor of claim 11 wherein the metrics comprise an oxygen saturation difference between tissue sites and wherein the metrics are tested to determine if the oxygen saturation difference exceeds a threshold.

13. The monitor of claim 10 wherein the means for indicating comprises a plurality of colored indicators that, when illuminated, signal different likelihoods that the oxygen saturation measurements have detected a congenital heart disease condition.

14. The monitor of claim 13 further comprising means for grading an infant as to the potential for congenital heart disease based upon one or more of the visual and audio outputs.

\* \* \* \* \*